United States Patent
Ulmsten

(12) 
(10) Patent No.: US 6,491,703 B1
(45) Date of Patent: *Dec. 10, 2002

(54) SURGICAL INSTRUMENT FOR TREATING FEMALE URINARY INCONTINENCE

(75) Inventor: Ulf Ulmsten, Danderyd (SE)

(73) Assignee: Ethicon, Inc., Somerville, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/051,311

(22) PCT Filed: Oct. 8, 1996

(86) PCT No.: PCT/SE96/01269

§ 371 (c)(1),
(2), (4) Date: Jul. 27, 1998

(87) PCT Pub. No.: WO97/13465

PCT Pub. Date: Apr. 17, 1997

(30) Foreign Application Priority Data

Oct. 9, 1995 (SE) ................................. 9503512

(51) Int. Cl.[7] .............................................. A61B 17/04
(52) U.S. Cl. ....................................... 606/144; 606/139
(58) Field of Search .............................. 606/144, 148, 606/228–230, 222–227, 139, 119

(56) References Cited

U.S. PATENT DOCUMENTS

| | | |
|---|---|---|
| 3,182,662 A | 5/1965 | Shirodkar |
| 3,311,110 A | 3/1967 | Singerman et al. |
| 3,472,232 A | 10/1969 | Earl |
| 3,763,860 A | 10/1973 | Clarke |
| 3,858,783 A | 1/1975 | Kapitanov et al. |
| 3,924,633 A | 12/1975 | Cook et al. |
| 4,037,603 A | 7/1977 | Wendorff |
| 4,128,100 A | 12/1978 | Wendorff |
| 4,235,238 A | 11/1980 | Ogiu et al. |
| 4,441,497 A | 4/1984 | Paudler |
| 4,509,516 A | 4/1985 | Richmond |
| 4,946,467 A * | 8/1990 | Ohi et al. ................ 606/228 |
| 5,032,508 A | 7/1991 | Naughton et al. |
| 5,112,344 A | 5/1992 | Petros |
| 5,250,033 A * | 10/1993 | Evans et al. ............. 606/160 |
| 5,281,237 A | 1/1994 | Gimpelson |
| 5,368,595 A * | 11/1994 | Lewis ....................... 606/72 |
| 5,383,904 A * | 1/1995 | Totakura et al. .......... 606/228 |
| 5,403,328 A | 4/1995 | Shallman |
| 5,628,756 A * | 5/1997 | Barker, Jr. et al. ....... 606/139 |
| 5,899,909 A * | 5/1999 | Claren et al. ............. 606/119 |
| 5,935,122 A * | 8/1999 | Fourkas et al. ........... 604/523 |
| 5,945,122 A | 8/1999 | Abra et al. |

FOREIGN PATENT DOCUMENTS

| | | |
|---|---|---|
| AU | 278089 | 6/1965 |
| AU | 441561 | 1/1972 |
| DE | 4334419 | 4/1995 |
| EP | 0598976 | 6/1994 |
| WO | 9006567 | 3/1996 |

* cited by examiner

Primary Examiner—Gary Jackson

(57) ABSTRACT

The surgical instrument according to the present invention includes a tape that includes a netting enclosed by a thin plastic sheath such that insertion is facilitated while avoiding irritation or damage of body tissue. The surgical instrument further includes a shank having a handle at one end thereof, and a curved needle-like element, which is constructed to be connected with the shank to form a curved portion.

22 Claims, 5 Drawing Sheets

SURGICAL INSTRUMENT FOR TREATING FEMALE URINARY INCONTINENCE

FIELD OF THE INVENTION

The invention relates to a surgical instrument for treating female urinary incontinence.

BACKGROUND OF THE INVENTION

Document WO-A-9606567 discloses a surgical incontinence device that allows for alleviating female urinary incontinence while restoring continence by attaching two curved needles to a tape that is intended to be permanently implanted into the tissue between the vaginal wall and the abdominal wall of a patient, thus strengthening the tissue required to restore the urinary continence.

BRIEF SUMMARY OF THE INVENTION

The surgical instrument according to the present invention is an improvement over the instrument described hereinabove. More specifically, the surgical instrument comprises a tape that includes a netting enclosed by a thin plastic sheath such that insertion is facilitated while avoiding irritation or damage of body tissue. The surgical instrument further comprises a shank having a handle at one end thereof, and a curved needle-like element, which is constructed to be connected with the shank to form a curved portion.

BRIEF DESCRIPTION OF THE DRAWINGS

The invention will be explained in more detail with reference to the accompanying drawings which disclose the surgical instrument according to the invention and wherein.

DETAILED DESCRIPTION OF THE DRAWINGS

Figure 1:
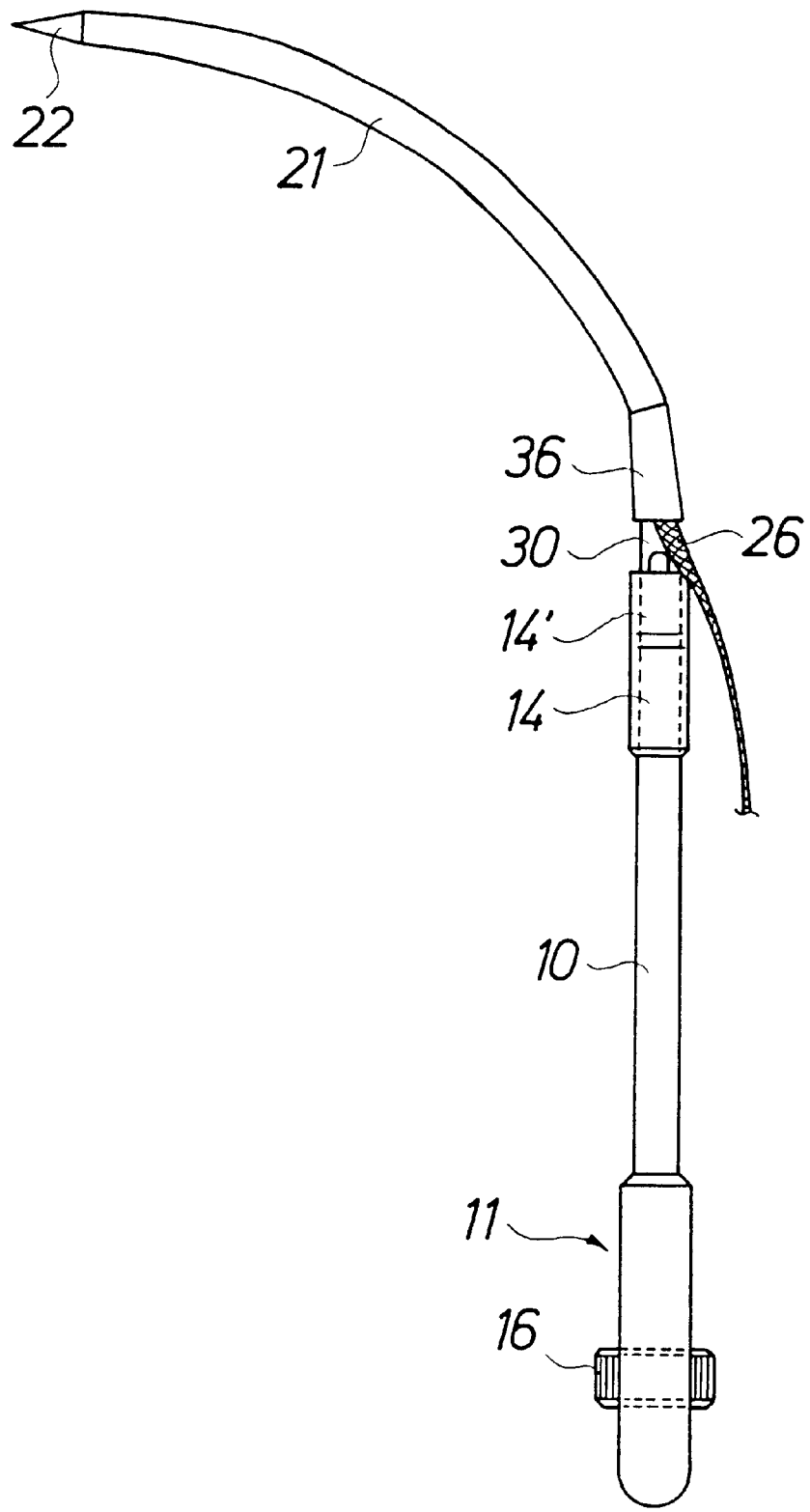
FIG. 1 is a side view of the surgical instrument according to the invention.

In the following description the same reference numerals have been used as in WO-A-9606567, for corresponding details of the instrument.

Figure 5:
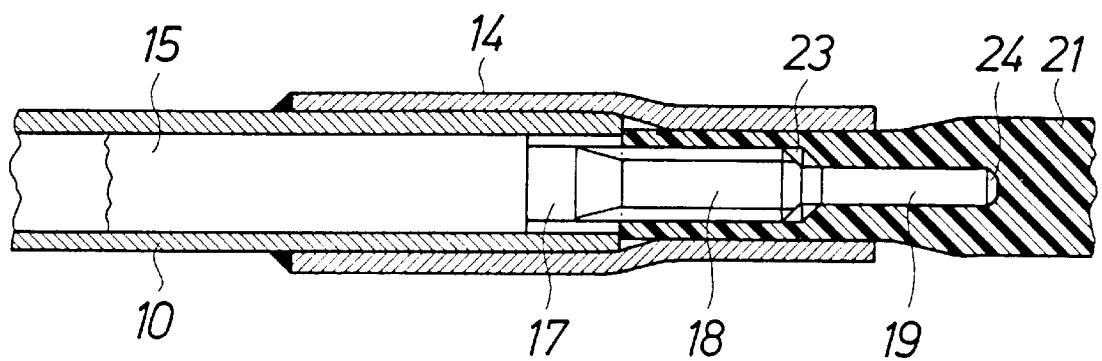
FIG. 5 is an enlarged fragmentary axial cross sectional view of a coupling of the instrument for connecting an exchangeable needle thereof.

The surgical instrument comprises a cylindrical tubular shank 10 having at one end thereof a handle 11. At the other end of the shank there is a socket 14. A cylindrical shaft 15 is rotatably mounted in the shank and can be rotated manually by means of a knob 16 mounted to one end of the shaft. The other end of the shaft forms a cylindrical portion 17, FIG. 5, of smaller outside diameter than the shaft, which joins a portion 18 having external threads, a smooth end portion 19 of further reduced diameter joining the threaded portion 18, end portion 19 forming a guide pin at said other end of the shaft. Portions 18 and 19 are received in the portion of socket 14 projecting from the shank. The surgical instrument as described so far is in agreement with the instrument disclosed in WO-A-960567 except that the end portion 14' of socket 14 is flattened from opposite sides (cfr FIGS. 1 and 2), so that the cross section of said end portion is non-circular.

The surgical instrument also includes an exchangeable and disposable needle 21 which at one end thereof is attached to the shank at one end of the needle and extends over substantially a quarter of a circle to the other, free end thereof in order to follow substantially the profile of the pubis between the vagina and the abdominal wall. The needle has uniform circular cross section and has a smooth, preferably polished outside surface. At the free end thereof the needle forms a point 22 by being terminated by a conical portion.

For attachment of needle 21 to shank 10 the needle forms at said one end thereof a straight portion 30 which is cylindrical but has milled flat faces 31 over that part of said portion 30, extending from the adjacent end of the needle, which shall be received by socket portion 14'. The needle should be oriented in a predetermined rotational position in relation to the shank, and more particularly it should project at right angles to the plane of handle 11. This rotational position is secured by the non-circular shape of socket portion 14' and the end portion of the needle having the flat faces 31, which fits into socket portion 14'. The end portion of the needle having the flat faces 31 joins the body of the needle over a conical portion 32, which tapers towards a shoulder 33.

An axial blind hole extends from the end surface of the needle said hole having a threaded portion 23 and inwardly thereof a narrower, cylindrical portion 24. Guide pin 19 is dimensioned to be guidingly received by said latter portion when the threaded portion 18 for attaching needle 21 to the rest of the surgical instrument is screwed into threaded portion 23 of the blind hole by rotating shaft 15 by manual rotation of knob 16, the end surfaces of the shank and the needle being pressed against each other. Also this attachment is in agreement with that described in WO-A-9606567.

Figure 2:
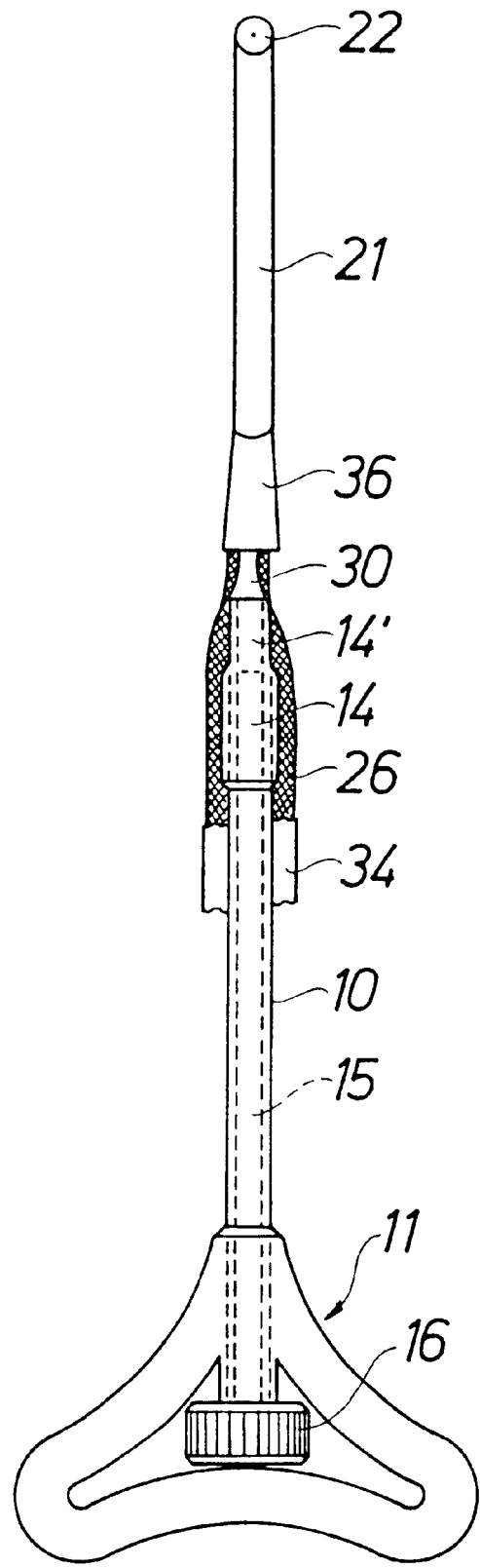
FIG. 2 is a plan view of the surgical instrument.
Figure 3:
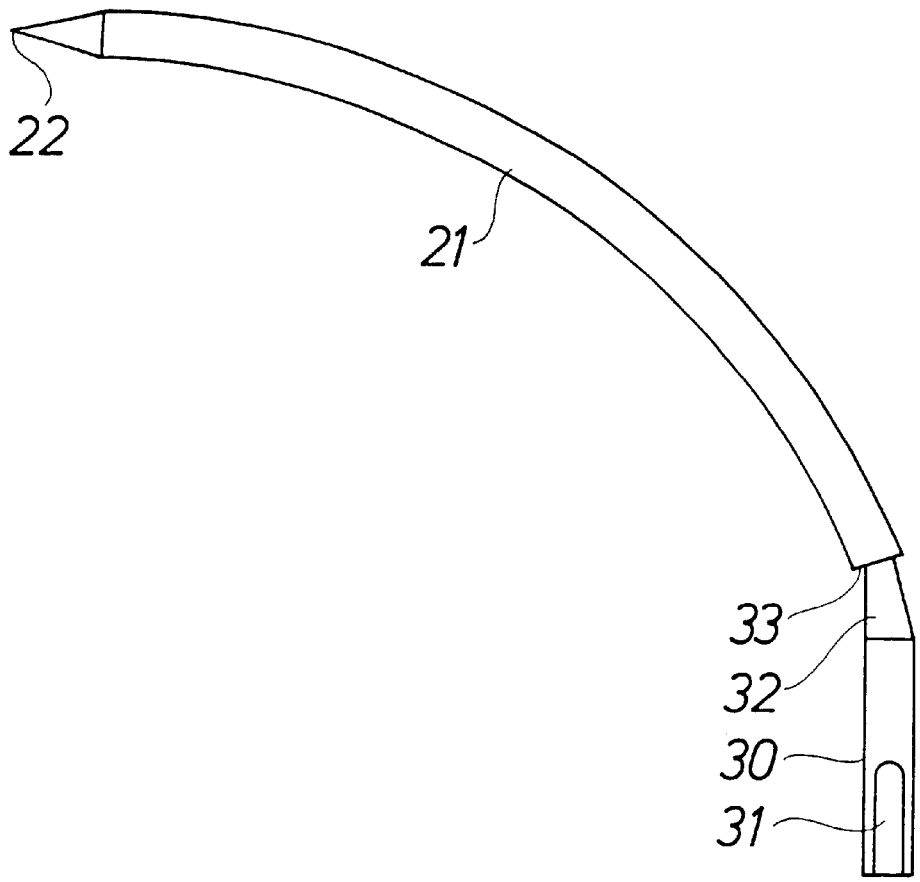
FIG. 3 is an exploded side view of one of the needles and tape and shrinkage hose to be connected with said needle.
Figure 3:
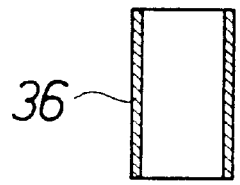
Figure 3:
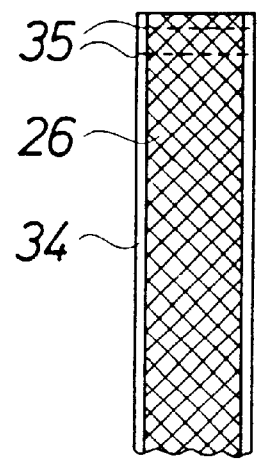
Figure 4:
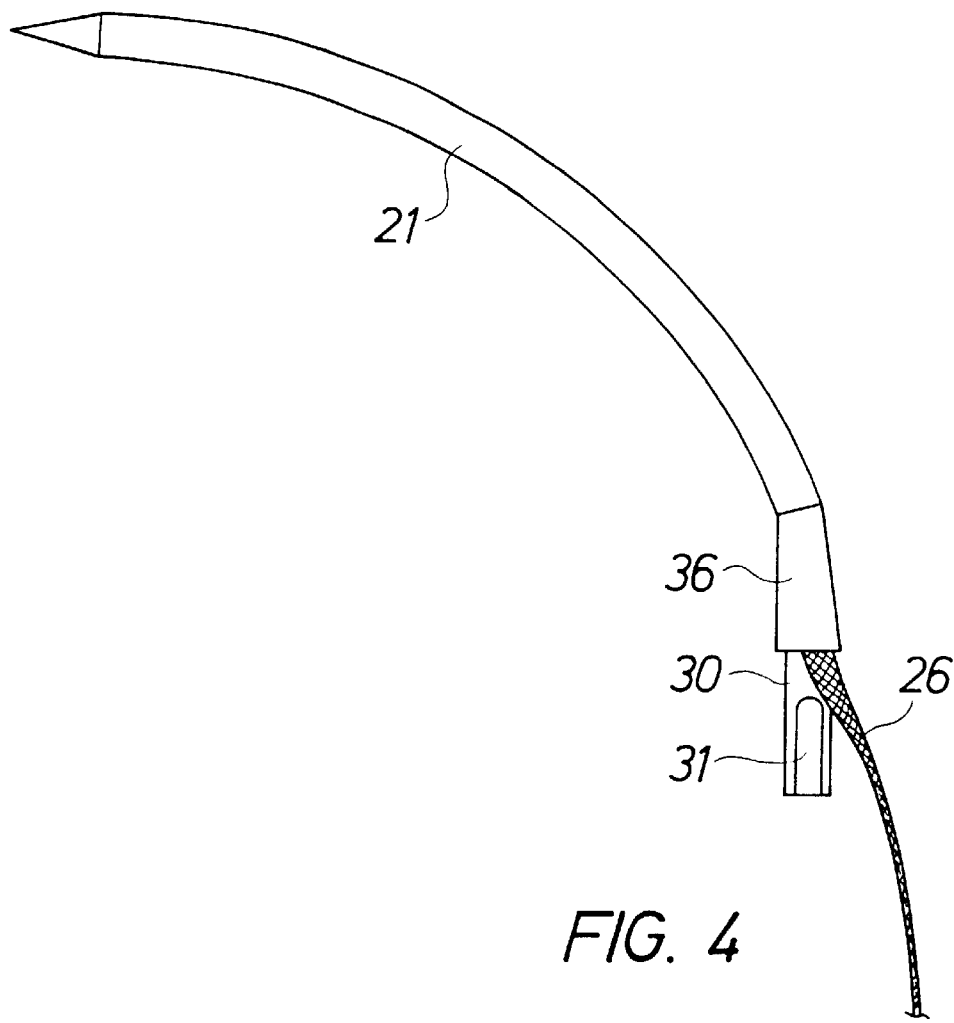
FIG. 4 is a side view of the needle in FIG. 3 with the tape connected therewith.
Figure 6:
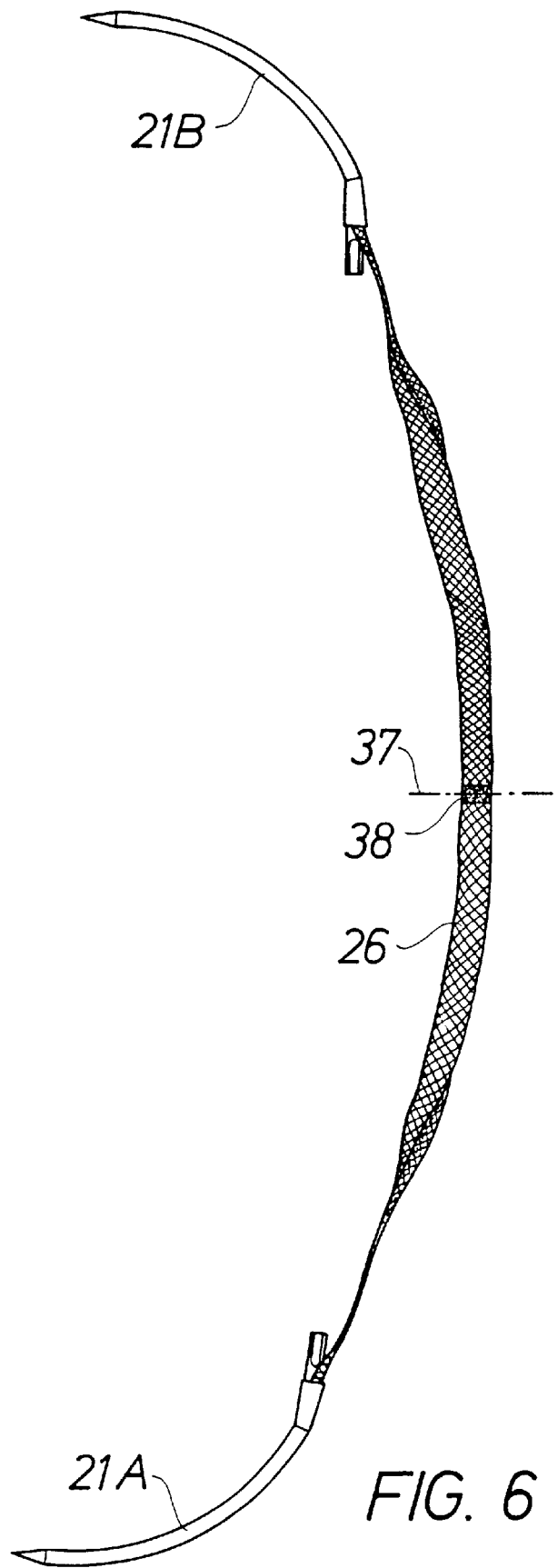
FIG. 6 is a side view of two needles and a tape interconnecting said needles.

When the method as described in WO-A-9606567 is practised two needles 21A and 21B, FIG. 6 of the embodiment described shall be connected one at each end of a tape 26. According to the present invention the tape of the preferred embodiment comprises a mesh or netting forming openings of the order of 1 mm. A suitable material for the tape is PROLENE®, a knitted polypropylene mesh having a thickness of 0,7 mm manufactured by Ethicon, Inc., Sommerville, N.J., USA. This material is approved by FDA in USA for implantation into the human body. The netting (tape) preferably has a width of approximately 10 mm and is enclosed in a thin polyethylene sheath 34 which in flattened condition has substantially the same width as the tape although a difference in width is shown in FIG. 2 in order to make the provision of the sheath more clear. The length of the netting should be approximately 400 mm. The netting and the sheath are interconnected by means of two rows 35 of stiching. The end portion of the sheath is attached to the conical portion 32 of the needle by means of a suitable strong glue, and the interconnection of the needle and sheath is covered by a shrink hose 36 of rubber which extends from the shoulder 33 over the conical portion 32 and partly over the cylindrical end portion 30 of the needle. The shrink hose is substantially flush with the surface of the needle at the shoulder. By this arrangement the netting is securely attached to the needle.

The purpose of sheath 34 is above all to facilitate the insertion of the netting in the manner described in WO-A-

06567, i.e. when the netting is pulled at the ends thereof from the vaginal wall to the abdominal skin and to avoid that rough edges of the netting irritate or damage the body tissues.

When the tape has been positioned in the correct position as a sling around the urethra the polyethylene sheath shall be removed, and in order to facilitate the removal the sheath should be perforated at the longitudinal center thereof as indicated by a dot-and-dash line 37 in FIG. 6, so that the two halves of the sheath can be withdrawn from the body by pulling at the respective outer ends thereof the halves being separated at the perforation under the influence of the pulling force.

The purpose of the polyethylene sheath is also to protect the netting during attachment to the needles and during handling before and during insertion into the body.

The longitudinal center of the tape and sheath should be indicated by a visible color mark 38, FIG. 6 so that the surgeon readily can see when the netting is symmetrically located with reference to urethra during the surgery.

What is claimed is:

1. Surgical instrument for treating female urinary incontinence, comprising
    a shank having a proximal end and a distal end,
    a handle at the proximal end of said shank,
    a tape to be implanted into the body as a loop around urethra, said tape including a netting enclosed by a sheath that can be withdrawn from the tape after the tape is inserted within the body,
    two curved needles, each having a proximal end and a distal end, wherein the proximal end of each needle is connected to an end of the tape, and
    means on said shank and each of said needles for exchangeable connection of the proximal end of the needles one at a time to the distal end of the shank to form an extension of the shank as a curved end portion thereof.

2. Surgical instrument as in claim 1, wherein said netting is made of polypropylene.

3. Surgical instrument as in claim 1, wherein said sheath is made of polyethylene.

4. Surgical instrument as in claim 1, wherein said sheath has a perforation line at a longitudinal center thereof.

5. Surgical instrument as in claim 1, wherein the netting and the sheath are interconnected by stitching.

6. Surgical instrument as in claim 1, wherein the netting and the sheath are connected to the needle by gluing to a conical portion at said proximal end of the needle.

7. Surgical instrument as in claim 6, further comprising a shrink hose covering said netting and said sheath at the site of attachment thereof.

8. Surgical instrument as in claim 7, wherein one end of the shrink hose abuts a shoulder distal to said conical portion and has its outside surface substantially at the level of the surface of the needle at said shoulder.

9. Surgical instrument as in claim 1, wherein a visible marking is provided on the sheath at a longitudinal center thereof.

10. Surgical instrument for treating female urinary incontinence, comprising a tape to be implanted into the body as a loop around urethra, said tape enclosed by a sheath that can be withdrawn from the tape after the tape is implanted in the body, and
    two curved needles, each having a proximal end and a distal end, wherein the proximal end of each needle is connected to an end of the tape.

11. Surgical instrument for treating female urinary incontinence, comprising, in combination, a substantially flat, flexible tape adapted to be implanted into a female patient's body as a supportive loop beneath an urethra; and a flexible sheath having a first portion covering a first length of said tape and removably applied to one end of said tape and a second portion covering a second length of said tape and removably applied to an opposite end of said tape, said first and second portions cooperating to substantially cover the entire length of said tape prior to implantation of the tape and sheath combination into a patient's body, said sheath being removable from said tape after the implantation of said tape and sheath combination.

12. Surgical instrument as in claim 11, wherein said sheath is made of polyethylene.

13. Surgical instrument as in claim 11, wherein said sheath includes a perforation line intermediate opposite ends of said sheath, said perforation line being oriented transversely relative to a longitudinal axis of said tape.

14. Surgical instrument as in claim 13, wherein said perforation line bifurcates said sheath into two portions, each of which is independently removable from said tape after the implantation of said tape and sheath combination.

15. Surgical instrument as in claim 11, wherein said sheath includes a visible marking at a longitudinal center thereof.

16. Surgical instrument as in claim 11, wherein said tape is in the form of a netting.

17. Surgical instrument as in claim 16, wherein said netting is made of polypropylene.

18. Surgical instrument as in claim 16, wherein said netting and said sheath are interconnected by stitches at an attachment site.

19. Surgical instrument as in claim 18, further comprising a shrink hose covering said netting and said sheath at said attachment site.

20. Surgical instrument as in claim 11, wherein said flexible tape and said flexible sheath move conjointly during implantation and prior to the removal of said sheath from said tape.

21. Surgical instrument for treating female urinary incontinence, comprising a tape to be implanted into a female patient's body as a loop beneath an urethra, said tape being in the form of a netting; and a sheath enclosing said tape and removably applied to said tape, whereby said sheath can be removed from said tape after said tape is implanted in the body, said netting and said sheath being interconnected by stitches at an attachment site.

22. Surgical instrument as in claim 21, further comprising a shrink hose covering said netting and said sheath at said attachment site.

* * * * *

UNITED STATES PATENT AND TRADEMARK OFFICE
CERTIFICATE OF CORRECTION

PATENT NO. : 6,491,703 B1
DATED : December 10, 2002
INVENTOR(S) : Ulf Ulmsten

It is certified that error appears in the above-identified patent and that said Letters Patent is hereby corrected as shown below:

Column 1,
Line 5, insert before "FIELD OF THE INVENTION":
-- CROSS REFERENCE TO RELATED APPLICATIONS
This application is the U.S. National stage under U.S.C. 371 of application No. PCT/SE96/01269 filed October 8, 1996, respectively. --.

Signed and Sealed this

Thirty-first Day of January, 2006

JON W. DUDAS
*Director of the United States Patent and Trademark Office*